United States Patent [19]

Hansen et al.

[11] Patent Number: 4,578,462
[45] Date of Patent: Mar. 25, 1986

[54] PROCESS FOR THE MANUFACTURE OF OPTICALLY ACTIVE COMPOUNDS

[75] Inventors: Hans-Jürgen Hansen, Riehen; Rudolf Schmid, Basel; Max Schmid, Brugg, all of Switzerland

[73] Assignee: Hoffmann-La Roche Inc., Nutley, N.J.

[21] Appl. No.: 525,529

[22] Filed: Aug. 22, 1983

[30] Foreign Application Priority Data

Aug. 27, 1982 [CH] Switzerland .................. 5110/82
Jul. 1, 1983 [CH] Switzerland .................. 3642/83

[51] Int. Cl.$^4$ .................. C07C 93/10; C07D 295/08
[52] U.S. Cl. .................. 544/177; 544/398; 546/236; 546/248; 548/574; 564/346; 564/508; 568/436; 568/449; 568/485; 556/413
[58] Field of Search .................. 544/177, 398; 546/236, 546/248; 548/574; 564/346, 508; 556/413

[56] References Cited

U.S. PATENT DOCUMENTS

2,541,091  2/1951  Oroshnik .................. 564/346
4,041,058  8/1977  Cohen et al. .................. 549/408

OTHER PUBLICATIONS

European Publication No. 0 068 506 (1-1983).
Oroshnik et al., J. Am. Chem. Soc., vol. 72 (1950) pp. 4608-4613.
Ohsugi et al., Biol. Chem., vol. 38 (1974) pp. 1925-1928.
Mornet et al., C.R. A cad. Sc., Ser. C, 279 (1974) pp. 229-232.
Mornet et al., J. Organomet. Chem., vol. 86 (1975) pp. 57-67.
Mornet et al., Bull. Chem. Soc. Fr., (1977) pp. 737-741.
Mornet et al., Synthesis, (1977) pp. 786-787.
Mornet et al., Tetrahedron Lett. (1977) pp. 167-174.

*Primary Examiner*—Robert W. Ramsuer
*Attorney, Agent, or Firm*—Jon S. Saxe; Bernard S. Leon; George W. Johnston

[57] ABSTRACT

The manufacture of optically active bifunctional compounds of the general formula

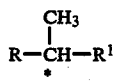

wherein R represents protected hydroxymethyl, protected formyl or alkoxycarbonyl and $R^1$ represents a group of the formula

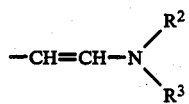

or $-CH_2-CH=NR^2$ in which $R^2$ and $R^3$ represent lower alkyl or cycloalkyl or $R^2$ and $R^3$ together with the nitrogen atom represent a heterocyclic ring, by isomerizing compounds of the general formula

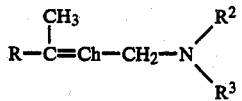

wherein R, $R^2$ and $R^3$ have the above significance and $R^3$ can additionally signify hydrogen, is described.

The compounds of formula I are potential intermediates in the manufacture of, inter alia, natural vitamin E and natural vitamin $K_1$.

10 Claims, No Drawings

PROCESS FOR THE MANUFACTURE OF OPTICALLY ACTIVE COMPOUNDS

The present invention concerns a novel process for producing optically active enamines or imines which are useful as intermediates for natural vitamin E, natural vitamin $K_1$ or of odorant substances.

SUMMARY OF THE INVENTION

The present invention concerns a process for preparing optically active compounds of the formula

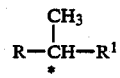                I wherein R is a protected hydroxymethyl, protected formyl or alkoxycarbonyl; and $R^1$ is

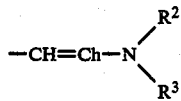                (Ia)

or $-CH_2-CH=NR^2$ (Ib) in which $R^2$ and $R^3$ individually are lower alkyl or cycloalkyl or $R^2$ and $R^3$ taken together with the nitrogen atom of Ia are a heterocyclic ring.

To produce Compound I in accordance with the invention, an amine of the formula

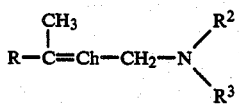                II wherein R, $R^2$ and $R^3$ are as above and $R^3$ can also be hydrogen, is isomerized in the presence of a complex of a metal of Group VIII with (a) an optically active compound of the formula, which is present in the (R)- or (S)-form,

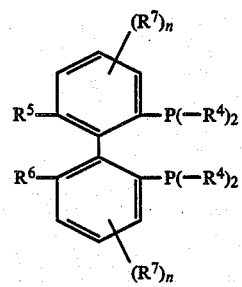                III wherein $R^4$ is phenyl; $R^5$ and $R^6$ individually are hydrogen, lower alkyl, lower alkoxy, di-lower alkylamino or protected hydroxymethyl or $R^5$ and $R^6$ taken together are $(-CH_2-)_m$, $-CH_2-O-CH_2-$,

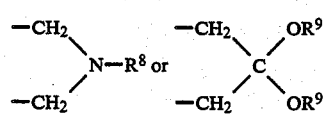

in which m is an integer 3, 4 or 5; $R^8$ is lower alkyl, phenyl or benzyl; $R^9$ is lower alkyl or both $R^9$ moieties taken together are dimethylene or trimethylene; $R^7$ is methyl, lower alkoxy, di-lower alkylamino or fluorine; and n is an integer 0, 1, 2 or 3, or (b) an optically active compound which is present in the (R)- or (S)-form, of the formula

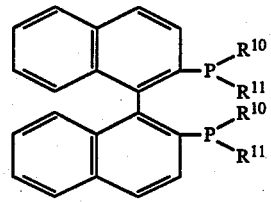                IV wherein $R^{10}$ and $R^{11}$ individually are phenyl or cyclohexyl and the naphthalene rings in compound IV are individually unsubstituted or substituted in the ortho-position with methyl, ethyl, halogen, di-lower alkylamino or lower alkoxy, so as to form Compound I.

The invention is also concerned with the novel optically active enamines and imines of formula I above and with their use for the manufacture of, for example, natural vitamin E, natural vitamin $K_1$ or of odorant substances.

DETAILED DESCRIPTION OF THE INVENTION

The present invention is concerned with a novel process for preparing optically active enamines or imines, which are functionalized in the 4-position, of the formula

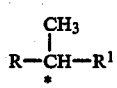                I wherein R is a protected hydroxymethyl, protected formyl or alkoxycarbonyl; and $R^1$ is

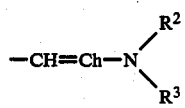                (Ia)

or $-CH_2-CH=NR^2$ (Ib) in which $R^2$ and $R^3$ individually are lower alkyl or cycloalkyl or $R^2$ and $R^3$ taken together with the nitrogen atom of Ia are a heterocyclic ring;

which process comprises isomerizing a compound of the formula

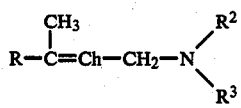                II wherein R, $R^2$ and $R^3$ are as above and $R^3$ can also be hydrogen, in the presence of a catalytic complex. The complex comprises a metal of Group VIII with (a) an optically active compound of the formula, which is present in the (R)- or (S)-form

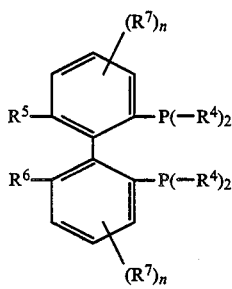

wherein R[4] is phenyl, R[5] and R[6] individually are hydrogen, lower alkyl, lower alkoxy, di-lower alkylamino or protected hydroxymethyl or R[5] and R[6] taken together are (—CH$_2$—)$_m$, —CH$_2$—O—CH$_2$—,

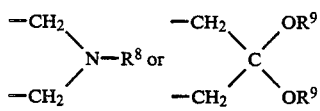

in which m is an integer 3, 4 or 5; R[8] is lower alkyl, phenyl or benzyl; R[9] is lower alkyl or both R[9] moieties taken together are dimethylene or trimethylene; R[7] is methyl, lower alkoxy, di-lower alkylamino or fluorine; and n is an integer 0, 1, 2 or 3, or (b) an optically active compound of the formula which is present in the (R)- or (S)-form

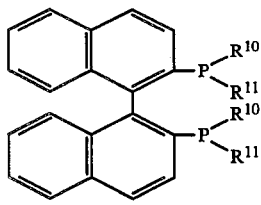

wherein R[10] and R[11] individually are phenyl or cyclohexyl and the naphthalene rings in compound IV are individually unsubstituted or substituted in the ortho-position with methyl, ethyl, halogen, di-lower alkylamino or lower alkoxy.

The compounds of formula I can be hydrolyzed readily in a known manner to optically active aldehydes of the formula

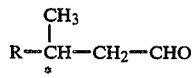

wherein R has the above significance.

These aldehydes, or acids or alcohols derived therefrom, are known compounds or analogues or derivatives of known compounds which can be prepared by conventional techniques. All these compounds, in turn, can be converted in a known manner into natural vitamin E or natural vitamin K$_1$.

Processes for the manufacture of optically active compounds of formula V or of analogues thereof are already known from German Offenlegungsschrift (DOS) No. 27 20 775 (corresponding to U.S. Pat. No. 4,138,289) and from European Patent Publication No. 39,830. In accordance with the above DOS these compounds are manufactured with high optical purity, but in a microbiological manner. In accordance with the process of the aforementioned European Patent Publication these compounds are obtained with an optical purity of merely about 60%.

There accordingly exists a need for a chemical, especially a catalytic, process for the manufacture of the optically active compounds of formulae I or V in accordance with which these compounds can be obtained especially with a high optical purity. This is now possible, since in accordance with this process such compounds are obtained with an optical purity of up to 99%. This novel process and also the novel compounds of formula I accordingly represent a valuable advance in the state of the art.

As used herein, alkyl denotes straight or branched chain saturated aliphatic hydrocarbon groups of 1 to 20 carbon atoms. Lower alkyl denotes alkyl groups of 1 to 4 carbon atoms such as methyl, ethyl, propyl, isopropyl, n-butyl, isobutyl and tert.butyl.

Alkoxy as well as any other groups in the specification containing "alkyl" (eg. di-lower alkyl amino) denote moieties which their alkyl portions are as previously defined. Lower alkoxy as well as any other groups in the specification containing "lower alkoxy" (eg. lower alkoxylcarbonyl) denote moieties which their lower alkyl portion are as previously defined. Alkoxycarbonyl are preferably alkoxy-carbonyl groups in which their alkyl moiety contains 1–4 carbon atoms such as methoxycarbonyl, ethoxycarbonyl and the like.

Cycloalkyl denotes a mononuclear hydrocarbon ring of 3 to 8 carbon atoms. Preferably cycloalkyl denotes rings of 3 to 6 carbon atoms (eg cyclopropyl, cyclopentyl, cyclohexyl and the like).

A heterocyclic ring denotes a mononuclear hydrocarbon ring of 3 to 8 carbon atoms containing one or more hetero atoms (eg. S, N, O). Where R[2] and R[3] together with the nitrogen atom in moiety Ia of compound I represent a heterocyclic ring, this is preferably a pyrrolidine or piperidine ring. In such ring there can, however, also be present a further oxygen atom or an optionally alkylated (C$_1$-C$_4$) or benzylated nitrogen atom (e.g. the morpholine or piperazine ring).

Aryl denotes mononuclear and polynuclear aromatic hydrocarbon groups which can be unsubstituted or substituted in one or more positions with halogen, nitro, alkylthio, acyloxy, alkoxyalkoxy, lower alkylenedioxy, lower alkyl or lower alkoxy. Suitable mononuclear aromatic hydrocarbon groups are phenyl and the like. Typical polynuclear aromatic hydrocarbon groups are napthyl, anthryl, phenanthryl, azulyl and the like.

Protected hydroxymethyl is a radical of the formula

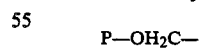

wherein P is any conventional ether-forming group such as aryl methyl (eg. benzyl), methyl, tert.butyl, allyl, methoxy-methyl and the like, as well as any conventional silyl ether-forming group such as tri-lower alkyl silyl (eg. trimethylsilyl, tert.butyl dimethyl-silyl and the like.)

Protected formyl denotes any conventional group used to protect aldehydes during isomerization. Typical protected formyl groups are acetals, that is, acetalized formyl groups. Acetalized formyl groups are, for example, groups of the formula

in which A is $C_1$-$C_4$-alkyl or both A moieties taken together are $C_2$-$C_4$-alkylene. Preferred A moieties are methyl and ethyl. Both A moieties taken together preferably are ethylene or trimethylene.

Unless otherwise stated, all appropriate formulae include E/Z mixtures as well as corresponding E and Z stereoisomers.

The asterisk in the formulae denote a chiral center for an optically active compound.

In the scope of the present invention, the aforementioned phenyl and benzyl groups can be not only unsubstituted, but also substituted in the ortho-, meta- or para-position or also multiply substituted. As substituents there come into consideration lower alkyl or lower alkoxy groups, preferably methyl or methoxy groups, di-lower alkyl-amino groups, preferably dimethylamino groups, as well as fluorine.

Preferred compounds of formula III are those in which $R^4$ signifies unsubstituted phenyl or phenyl substituted with methyl or fluorine, $R^5$ and $R^6$ are the same and signify lower alkyl or $R^5$ and $R^6$ together signify the group —$CH_2$—O—$CH_2$—, n signifies the number 0 or 1 and $R^7$ signifies methyl, fluorine or di-lower alkylamino.

In accordance with the invention the isomerization of a compound of formula II to a compound of formula I is carried out with the aid of a catalyst complex of a metal of Group VIII with a ligand of formula III or IV. Preferred metals of Group VIII are rhodium, iridium and cobalt, especially rhodium.

The aforementioned catalyst complexes are for the most part novel, but they can be prepared in a manner which is simple and known. This is carried out, for example, by reacting a compound of formula III or IV with a compound which can yield metal of Group VIII in a suitable inert solvent. This can be carried out on the one hand by bringing the phosphorous compounds of formulae III and IV as such, in a solution of a compound of formula II to be isomerized, into contact with a compound which yields a metal of Group VIII; i.e. the catalyst complex can be formed in situ. On the other hand, the phosphorus compounds of formulae III and IV can firstly be reacted in a suitable organic or aqueous solvent with a compound which yields a metal of Group VIII to give the corresponding catalyst complex. This complex can then be added to a solution of the compound of formula II to be isomerized. The latter method is preferred. Compounds which can yield a metal of Group VIII are known. Suitable compounds include Group VIII metal tri-halide hydrates and Group VIII metal sulphates (eg., to yield rhodium: rhodium trichloride hydrate, rhodium tribromide hydrate and rhodium sulphate) or also organic Group VIII complexes with alkenes (eg. ethylene, propene and the like) as well as with bis-olefins, (eg. 1,5-cyclooctadiene, 1,5-hexadiene, bicyclo[2.2.1]-hepta-2,5-diene) or with other dienes which form readily soluble complexes with Group VIII metals. Preferred compounds which yield rhodium are, for example, di-μ-chloro-bis[$\eta^4$-1,5-cyclooactadiene]dirhodium (I) or di-μ-chloro-bis[$\eta^4$-norbornadiene]dirhodium (I).

Other suitable compounds which yield one of the other metals of group VIII are, for example, iridium trichloride hydrate, di-μ-chloro-bis[$\eta^4$-1,5-cyclooctadiene]diiridium (I); cobalt dichloride, cobalt (II) acetate or naphthenate, cobalt II or cobalt (III) acetylacetonate and the like.

Not only the reaction of the phosphorus compounds of formulae III and IV with a compound which yields a metal of Group VIII, but also the aforementioned isomerization can be carried out in suitable organic solvents which are inert under the reaction conditions. Especially suitable organic solvents are lower alkanols such as, for example, methanol or ethanol, aromatic hydrocarbons such as benzene or toluene, cyclic ethers such as tetrahydrofuran or dioxan, esters such as, for example, ethyl acetate or mixtures thereof and the like. Furthermore, the complex formations can be carried out in aqueous medium or also in dichloromethane.

The ratio between the metal of Group VIII and the ligands of formulae III and IV conveniently lies between about 0.05 mol and about 5 mol, preferably between about 0.5 mol and about 2 mol of metal per mol of ligand of formula III or IV.

The amount of metal in the complexes of the Group VIII metal with the ligands of formulae III and IV, based on the compounds II to be isomerized, conveniently lies between about 0.01 mol % and about 2 mol %, preferably between about 0.05 mol % and about 1 mol % and especially between about 0.1 mol % and about 0.5 mol %.

The isomerization can conveniently be carried out in an inert organic solvent and at a temperature from about room temperature (23° C.) to about 130° C. This reaction is preferably carried out at an elevated temperature, i.e. depending on the solvent used either at the reflux temperature of the reaction mixture or in a closed vessel under pressure.

The compounds of formula II are known compounds or derivatives or analogues of known compounds which can be prepared readily in a known manner. They can be present as (E/Z) mixtures, but are preferably present in the pure (E)- or (Z)-form.

The optically active compounds of formula III are novel compounds. They can be prepared, for example, by reacting a racemic compound of the formula

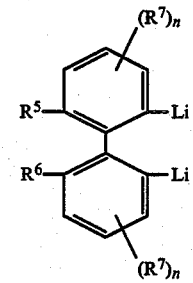

wherein $R^5$, $R^6$, $R^7$ and n have the above significance, with a compound of the formula

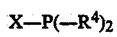

wherein $R^4$ has the above significance and X represents a leaving group,
and resolving a racemic compound of formula III obtained into the optical antipodes.

The term "leaving group" signifies in this connection any conventional leaving group especially groups such as, for example, halogen, (especially chlorine or bromine) as well as alkoxy groups such as methoxy, and the like.

The reaction of a compound of formula VI with a compound of formula VII can be carried out in a known manner. The reaction is conveniently carried out in an inert aprotic organic solvent such as, for example, an ether (e.g. diethyl ether, tetrahydrofuran, dimethoxyethane and the like). The reaction is also conveniently carried out at a temperature from about room temperature to about −120° C., preferably below about −60° C. and especially below about −90° C. The pressure is not critical and the reaction can be carried out readily at atmospheric pressure.

The resolution of a racemic compound of formula III into the optical antipodes can be carried out in a known manner. It is preferably carried out, for example, by complex formation with di-$\mu$-chloro-bis[(R)-2-[1-dimethylamino)ethyl]phenyl-C,N]-dipalladium (II), separation of the two diastereomeric complexes by fractional crystallization and subsequent reductive liberation of the corresponding antipodes.

The racemic compounds of formula VI and the compounds of formula VII are known compounds or analogues of known compounds which can be prepared readily in a known manner.

The following examples illustrate the preparation of the compounds provided by the invention. Unless otherwise stated, percentages and ratios relating to solvent mixtures are expressed in volume and the remaining percentages and ratios are expressed in weight. Temperatures are in degrees Celsius (°C.), and room temperature is about 23° C. The ether is diethyl ether. Unless indicated otherwise, the Examples were carried out as written.

EXAMPLE 1

(A) 2.3 g (10.8 mmol) of (E)-N,N-diethyl-4-tert.butoxy-3-methyl-2-butenylamine, 10 ml of dry tetrahydrofuran and 49 mg (0.059 mmol=0.55 mol%) of [$\eta^4$-bicyclo[2.2.1]hepta-2,5-diene][(R)-(6,6'-dimethyl-2,2'-biphenylylene)-bis(diphenylphosphine)]rhodium (I) tetrafluoroborate were placed in a Pyrex bomb tube having a capacity of about 25 ml. After degasifying the mixture, the tube was sealed and heated at 110° C. for 24 hours in a bomb tube oven. The dark brown mixture was evaporated and the brown oily residue was distilled at about 150° C./15 Torr in a bulb-tube. The light yellowish distillate obtained (1.80 g) contained 68% of (1E,3R)-N,N-diethyl-4-tert.butoxy-3-methyl-1-butenylamine according to gas chromatography.

(B) The previously obtained distillate was taken up in 13.5 ml of tetrahydrofuran, treated with 6.5 ml of 0.5N hydrochloric acid and 2 ml of acetic acid. The homogeneous mixture was stirred at 0° C. for 15 minutes. For the working-up, the mixture was poured into water and extracted three times with ether. The combined organic extracts were washed twice with 1N hydrochloric acid, then with dilute sodium bicarbonate solution and saturated sodium chloride solution, dried over sodium sulphate, filtered and evaporated. After bulb-tube distillation of the resulting oil at about 100° C./15 Torr, there were obtained 1.03 g of (R)-4-tert.butoxy-3-methyl-butanal as a colourless oil having a purity of 97% according to gas chromatography; $[\alpha]_D^{20} = +23°$ (c=4.98% in CHCl$_3$). The absolute configuration was determined and an optical purity of about 93% was estimated by chemical correlation with (R)-3-methyl-$\gamma$-butyrolactone.

In a manner analogous to the foregoing, using [$\eta^4$-bicyclo[2.2.1]hepta-2,5-diene][(S)-6,6'-diemthyl-2,2'-biphenylylene)-bis(diphenylphosphine)]rhodium (I) tetrafluoroborate as the catalyst there was obtained (1E, 3S)-N,N-diethyl-4-tert.butoxy-3-methyl-1-butenylamine; purity according to gas chromatography 79%; $[\alpha]_D^{20} = -4.65°$ (c=5% in CHCl$_3$). The corresponding (S)-4-tert.butoxy-3-methyl-butanal was prepared as described previously; purity according to gas chromatography 99%; $[\alpha]_D^{20} = -25.3°$ (c=4.9% in CHCl$_3$).

The enantiomeric purity (ee) was determined in analogy to the method of D. Valentine, Jr. et al., in J. Org. Chem. 41, 62 (1976) by oxidation to the acid, amide formation with (R)-$\alpha$-methyl-4-nitrobenzylamine and analysis of the diastereomeric amides by means of gas chromatography or liquid chromatography. There was thus found a SR/RR diastereomer ratio of 96.3:3.7, from which a value of 92.6% was derived for the enantiomeric purity.

EXAMPLE 2

The [$\eta^4$-bicyclo[2.2.1]hepta-2,5-diene][(R)-(6,6'-dimethyl-2,2'-biphenylylene)-bis(diphenylphosphine)]rhodium (I) tetrafluoroborate used in Example 1 was prepared as follows.

(A) 680 mg (2 mmol) of (RS)-2,2'-dibromo-6,6'-dimethyl-biphenyl were placed under argon gasification in a 100 ml sulphonation flask provided with a dropping funnel, thermometer, rubber septum and magnetic stirrer and 20 ml of absolute diethyl ether were injected in by means of a syringe. The resulting solution was cooled to about −90° to −100° C. and at this temperature treated dropwise with 5.6 ml of an about 1.4M tert.butyl lithium solution in pentane (8 mmol). The mixture was stirred at about −100° C. for a further 20 minutes, whereby it slowly became whitish and turbid. A solution of 880 mg (4 mmol) of chlorodiphenylphosphine in 5 ml of absolute diethyl ether was then introduced dropwise at about −90° to −100° C. within 15 minutes. The mixture was left to warm to room temperature during 2 hours, the separation of a white precipitate setting in at about −60° C., and stirred at room temperature for a further 1 hour. For the working-up, the mixture was treated under argon with water and dichloromethane, the organic phase was separated, washed with water and dried by filtration over sodium sulphate. The crystalline residue obtained after evaporation was recrystallized from ethyl acetate and there were obtained 620 mg of (RS)-(6,6'-dimethyl-2,2'-biphenylylene)-bis-(diphenylphosphine) as white crystals with a melting point of 242°-243° C. From the mother liquor there were obtained after crystallization from ethanol/toluene a further 84 mg of product with a melting point of 240°-242° C.; total yield 704 mg.

(B) The (RS)-2,2'-dibromo-6,6'-dimethyl-biphenyl used above was prepare as follows:

A solution of 2.77 g (40.1 mmol) of sodium nitrite in 5 ml of water was added dropwise at −5° to 0° C. within 2 hours to a solution of 4.24 g (20 mmol) of (RS)-6,6'-dimethyl-2,2'-biphenyldiamine in 12 ml of 48% aqueous hydrogen bromide solution. The ice-cold dark diazonium salt solution was transferred into a dropping funnel and added dropwise within 15 minutes to a hot (70°-75° C.) solution of 25 ml of a 2M copper (I) bromide solution in 48% aqueous hydrogen bromide solution. During the dropwise addition, the diazonium salt solution was held at 0° C. by the occasional additions of ice. After completion of the dropwise addition, the mixture was boiled at reflux for a further 5 minutes. The cooled solution was then extracted three times with 100 ml of ether each time. The combined organic extracts were washed twice with 50 ml 2N HCl each time, with 50 ml of saturated sodium bicarbonate solution each time and three times with 50 ml of water each time and then dried over sodium sulphate. The product (6 g) obtained after filtration and evaporation consisted according to gas chromatography of a 8:23:59 mixture of 2-bromo-6,6'-dimethyl-biphenyl, 2-bromo-2'-hydroxy-6,6'-dimethyl-biphenyl and (RS)-2,2'-dibromo-6,6'-dimethyl-biphenyl. Chromatography on silica gel [hexane/ether (9:1)] yielded 3.5 g of a 12:87 mixture of 2-bromo-6,6'-dimethyl-biphenyl and (RS)-2,2'-dibromo-6,6'-dimethyl-biphenyl, from which by two-fold recrystallization from pentane there were finally obtained 1.3 g of pure (RS)-2,2'-dibromo-6,6'-dimethyl-biphenyl with a melting point of 111°–112° C.

(C) A suspension of 2.49 g (4.52 mmol) of (RS)-(6,6'-dimethyl-2,2'-biphenylylene)-bis(diphenylphosphine) and 1.31 g (2.26 mmol) of di-μ-chloro-bis[(R)-2-(1-(dimethylamino)ethyl)phenyl-C,N]-dipalladium (II) in 100 ml of methanol was stirred at room temperature under argon until a homogeneous solution was obtained (about 4 hours). Thereto there was added dropwise a solution of 0.95 g (9.04 mmol) of ammonium tetrafluoroborate in 63 ml of water, the separation of a yellowish precipitate setting in after the addition of about 20 ml. The resulting precipitate was filtered off, washed with methanol/water (1:1) and dried over phosphorus pentoxide at 0.2 Torr, whereupon 1.79 g of yellowish crystals were obtained. The filtrate was diluted with 50 ml of water and stirred until the resulting precipitation coagulated (1 hour). Filtration and drying yielded a further 1.84 g of yellowish crystals; total yield 3.63 g.

The combined crystal fractions were dissolved in 150 ml of dichloromethane/diethyl ether (1:2). By the slow dropwise addition of 50 ml of hexane there was obtained a precipitate, 1.5 g of yellowish crystals being obtained after filtration. This material was recrystallized twice from 10 ml of dichloromethane by the portionwise addition of 10 ml of diethyl ether four times. In this manner there were obtained 1.07 g of [(R)-2-(1-(dimethylamino)ethyl)phenyl-C,N][(R)-(6,6'-dimethyl-2,2'-biphenylylene)-bis(diphenylphosphine)]palladium (II) tetrafluoroborate with a melting point of 213°–216° C.; $[\alpha]_D^{20} = +301.4°$ (c=1% in CHCl$_3$).

1 g (1.12 mmol) of the previously prepared tetrafluoroborate were introduced in small portions within 30 minutes at room temperature into a suspension of 42.6 mg (1.12 mmol) of lithium aluminium hydride in 15 ml of absolute tetrahydrofuran. The resulting black mixture was stirred for 1 hour. Thereafter, the reaction was interrupted by the addition of a few drops of saturated sodium chloride solution, the mixture was treated with active carbon and filtered over a bed of sodium sulphate and Celite, and rinsed four times with 10 ml of tetrahydrofuran each time. The black-brown residue resulting after evaporation of the filtrate was taken up in a small amount of dichloromethane and filtered over a short column of silica gel with dichloromethane. The yellow filtrate was evaporated and the crystalline residue was recrystallized from ethanol/toluene. There were obtained 121 mg of (R)-(6,6'-dimethyl-2,2'-biphenylylene)-bis(diphenylphosphine) as white crystals with a melting point of 210°–212.5° C.; $[\alpha]_D^{20} = -42.7°$ (c=1% in CHCl$_3$).

(D) 275 mg (0.5 mmol) of (R)-(6,6'-dimethyl-2,2'-biphenylylene)-bis(diphenylphosphine) and 115 mg (0.25 mmol) of di-μ-chloro-bis[η$^4$-bicyclo[2.2.1]hepta-2,5-diene]-dirhodium (I) were placed under argon in a Schlenk tube and treated with 4 ml of deoxygenated methanol. The mixture was stirred until a homogeneous red solution was obtained (1.5 hours). Thereto there was now added dropwise within 45 minutes a solution of 61 mg (0.55 mmol) of sodium tetrafluoroborate in 1.1 ml of deoxygenated water, an orange precipitate resulting. After stirring for a further 1 hour, the mixture was filtered under argon, the filter residue was washed twice with 0.5 ml of water each time and dried in a high vacuum. There were obtained 360 mg of [η$^4$-bicyclo[2.2.1]hepta-2,5-diene][(R)-(6,6'-dimethyl-2,2'-biphenylylene)-bis(diphenylphosphine)]rhodium (I) tetrafluoroborate as orange microcrystals with $[\alpha]_D^{20} = -35.9°$ (c=0.445% in CHCl$_3$).

In an analogous manner, there was prepared [η$^4$-bicyclo[2.2.1]hepta-2,5-diene][(S)-(6,6'-dimethyl-2,2'-biphenylylene)-bis(diphenylphosphine)]rhodium (I) tetrafluoroborate; $[\alpha]_D^{20} = -34°$ (c=0.54% in CHCl$_3$).

EXAMPLE 3

A Pyrex bomb tube was charged under nitrogen with 1.24 g (5.0 mmol) of (E)-N,N-diethyl-4-benzyloxy-3-methyl-2-butenylamine, 10 ml of tetrahydrofuran (distilled over sodium/benzophenone) and 49.8 g (0.058 mmol) of [η$^4$-1,5-cyclooctadiene][(S)-(6,6'-dimethyl-2,2'-biphenylylene)-bis(diphenylphosphine)]rhodium (I) perchlorate. After degasification, the tube was sealed and heated to 85° C. in a bomb tube oven for 58 hours. The dark brown mixture was evaporated and the residue was distilled in a bulb-tube at about 150° C./0.2 mmHg. There were thus obtained 1.05 g of a yellow oil which, according to gas chromatographic and NMR analysis, contained 73% of (1E,3S)-N,N-diethyl-4-benzyloxy-3-methyl-1-butenylamine; $[\alpha]_D^{20} = -5.1°$ (c=1.1% in hexane).

For the hydrolysis of the enamine, 0.85 g of the distillate was taken up in 6 ml of 50% acetic acid, the mixture was stirred vigorously for 10 minutes and then covered with 10 ml of hexane and stirred for a further 30 minutes. After separating the phases, the aqueous solution was extracted twice with ether. The combined organic phases were washed with 0.2N hydrochloric acid, saturated sodium bicarbonate solution and saturated sodium chloride solution, dried over sodium sulphate, filtered and evaporated. The residue was distilled in a bulb-tube at about 120° C./0.1 mmHg, there being obtained 0.43 g (54%) of (S)-4-benzyloxy-3-methylbutanal; purity according to gas chromatography ≧98%; $[\alpha]_D^{20} = -12.0°$ (c=4.06% in CHCl$_3$).

The determination of the enantiomeric purity was carried out as mentioned in Example 1 in analogy to the method of D. Valentine, Jr. and amounted to 98.8% ee.

A reaction of (E)-N,N-diethyl-4-benzyloxy-3-methyl-2-butenylamine with [η$^4$-1,5-cyclooctadiene][(R)-(6,6'-dimethyl-2,2'-biphenylylene)-bis(diphenylphosphine)]-rhodium (I) perchlorate carried out in a manner analogous to the foregoing, but at 75° C., yielded (R)-4-benzyloxy-3-methylbutanal with an enantiomeric purity of 99.2% ee; $[\alpha]_D^{20} = +12.05°$ (c=4.4% in CHCl$_3$).

EXAMPLE 4

The following compounds were prepared in a manner analogous to Example 3 (temperature 75° C.) using [η$^4$-1,5-cyclooctadiene][(R)-(6,6'-dimethyl-2,2'-biphenylylene)-bis(diphenylphosphine)]rhodium (I) perchlorate as the isomerization catalyst:

From (E)-4-benzyloxy-N,N-dibutyl-3-methyl-2-butenylamine the (1E,3R)-4-benzyloxy-N,N-dibutyl-3-methyl-1-butenylamine: purity according to gas chromatography 83%; $[\alpha]_D^{20}=+6.1°$ (c=2.13% in hexane). The corresponding (R)-4-benzyloxy-3-methylbutanal has an enantiomeric purity of 98.9% ee and a rotation $[\alpha]_D^{20}=+10.2°$ (c=2.7% in CHCl$_3$); purity according to gas chromatography 86%.

From 1-((E)-4-benzyloxy-3-methyl-2-butenyl)-piperidine the 1-((1E,3R)-4-benzyloxy-3-methyl-1-butenyl)-piperidine: purity according to gas chromatography 61%; $[\alpha]_D^{20}=+6.9°$ (c=2.15% in hexane). The corresponding (R)-4-benzyloxy-3-methylbutanal has an enantiomeric purity of 99.5% ee and a rotation $[\alpha]_D^{20}=+12.14°$ (c=3.6% in CHCl$_3$); purity according to gas chromatography 95%.

From 4-((E)-4-benzyloxy-3-methyl-2-butenyl)-morpholine the 4-((1E,3R)-4-benzyloxy-3-methyl-1-butenyl)-morpholine: purity according to gas chromatography 85%; $[\alpha]_D^{20}=+6.86°$ (c=2.15% in hexane). The corresponding (R)-4-benzyloxy-3-methylbutanal has an enantiomeric purity of 93.1% ee and a rotation $[\alpha]_D^{20}=+11.4°$ (c=3.63% in CHCl$_3$); purity according to gas chromatography 95%.

EXAMPLE 5

In a manner analogous to Example 3 (reaction temperature 80° C.), from (E)-N,N-diethyl-3-methyl-4-trimethylsiloxy-2-butenylamine there was obtained (1E,3R)-N,N-diethyl-3-methyl-4-trimethylsiloxy-1-butenylamine in the form of an oil; $[\alpha]_D^{20}=+17.1°$ (c=2.44% in hexane); purity according to gas chromatography 50%.

For the determination of the optical purity, 0.53 g of this oil was taken up in 5 ml of 0.5N hydrochloric acid and 2 ml of acetic acid. About 100 mg of sodium cyanoborohydride in portions of about 20 mg were added to the mixture within 1 hour while stirring well. After stirring for a further 2 hours, the mixture was made alkaline with 4N sodium hydroxide solution, saturated with potassium carbonate and then extracted continuously with ether for 18 hours. The residue from the ether extract was purified by chromatography on SiO$_2$ (ethyl acetate). After distillation in a bulb-tube at about 100°/0.02 mmHg, there were obtained 148 mg (50.5%) of (R)(+)-2-methyl-1,4-butanediol as a colourless oil; $[\alpha]_D^{20}=+14.0°$ (c=1.9% in MeOH); purity according to gas chromatography 99%.

For the antipode (S)(−)-2-methyl-1,4-butanediol there has been described a specific rotation $[\alpha]_D^{20}=-14.5°$ (c=0.6% in MeOH) [H. G. W. Leuenberger et al., Helv. Chim. Acta 62, 455 (1979)]. Therefrom there can be estimated an optical purity of about 96% for the (R)(+)-2-methyl-1,4-butanediol derived from the enamine.

In a manner analogous to the foregoing, from (E)-N,N-diethyl-4-(methoxymethoxy)-3-methyl-2-butenylamine there was obtained (1E,3R)-N,N-diethyl-4-(methoxymethoxy)-3-methyl-1-butenylamine; $[\alpha]_D^{20}=+4.6°$ (c=2.76% in hexane); purity according to gas chromatography about 40%. An optical purity of 94% was estimated for the corresponding (R)(+)-2-methyl-1,4-butanediol with a rotation of $[\alpha]_D^{20}=+13.6°$ (c=0.99% in methanol) and a purity according to gas chromatography of 85%.

EXAMPLE 6

In a manner analogous to Example 3, from (E)-4-allyloxy-N,N-diethyl-3-methyl-2-butenylamine there was obtained (1E,3R)-N,N-diethyl-3-methyl-4-(1-propenyloxy)-1-butenylamine; $[\alpha]_D^{20}=+17.3°$ (c=1.83% in hexane).

EXAMPLE 7

A Pyrex bomb tube was charged with 2.02 g (10 mmol) of (E)-N,N-diethyl-4,4-dimethoxy-3-methyl-2-butenylamine, 10 ml of tetrahydrofuran and 83.2 mg (0.10 mmol) of [η$^4$-bicyclo[2.2.1]hepta-2,5-diene][(S)-(6,6'-dimethyl-2,2'-biphenylylene)-bis(diphenylphosphine)]rhodium (I) tetrafluoroborate. After degasifying the mixture, the tube was sealed and heated at 90° C. for 56 hours in a bomb tube oven. The red-brown solution was evaporated and the residue was distilled in a bulb-tube at about 70°/0.2 mmHg. There was obtained (1E,3S)-N,N-diethyl-4,4-dimethoxy-3-methyl-1-butenylamine; purity according to gas chromatography 70%; $[\alpha]_D^{20}=-12.9°$ (c=4.05% in hexane). The corresponding (S)-4,4-dimethoxy-3-methylbutanal has a rotation $[\alpha]_D^{20}=-23.3°$ (c=4.66% in hexane); purity according to gas chromatography 96%.

The enantiomeric purity of this aldehyde was estimated to be ≧90% ee with a detection limit of 5% with the aid of NMR spectroscopy using the shift reagent tris[3-(heptafluoropropylhydroxymethylidene)-d-camphorato]-europium (III).

The (E)-N,N-diethyl-4,4-dimethoxy-3-methyl-2-butenylamine used as the starting material was prepared as follows:

A mixture of 56.4 g (0.30 mol) of 4-acetoxy-2-methyl-2-butenal dimethyl acetal, 150 ml of diethylamine, 675 mg (3 mmol) of palladium (II) acetate and 3.9 g (15 mmol) of triphenylphosphine was boiled under reflux for 15 hours under argon. After concentrating the mixture, the residue was suspended in 170 ml of ether/pentane (1:1), the solution was treated with active carbon, filtered over Hyflo and concentrated. The residual oil was firstly distilled at 40°–55°/0.3 mmHg over a 5 cm Vigreux column, there being obtained 57.1 g of N,N-diethyl-4,4-dimethoxy-3-methyl-2-butenylamine as a 90:10 (E/Z) mixture. This mixture was then fractionated over a 30 cm packed column. There were firstly obtained a total of 34.8 g (58%) of mixed fractions [(E/Z)=86:14] and then 14.5 g (24%) of pure (E)-N,N-diethyl-4,4-dimethoxy-3-methyl-2-butenylamine of boiling point 30°–32°/0.06 mmHg.

EXAMPLE 8

A Pyrex bomb tube was charged with 506 mg (2.73 mmol) of methyl 4-(diethylamino)-2-methyl-2-butenoate [83:17 (E/Z) mixture], 80 mg (0.0929 mmol) of [η$^4$-1,5-cyclooctadiene][(R)-(6,6'-dimethyl-2,2'-biphenylylene)-bis(diphenylphosphine)]rhodium (I) perchlorate and 8 ml of tetrahydrofuran, degasified, sealed and heated to 80° C. in a bomb tube oven for 64 hours. The brown-black mixture was evaporated and the residue was distilled in a bulb-tube at about 150°/15 mmHg. There were thus obtained 313 mg of a colourless oil which, in accordance with gas chromatographic analysis and NMR analysis, contained 53% of methyl (2R,3E)-4-(diethylamino)-2-methyl-3-butenoate and 32% of methyl 4-(diethylamino)-2-methyl-butyrate; $[\alpha]_D^{20} = -24.2°$ (c=2.35% in hexane).

The methyl 4-(diethylamino)-2-methyl-2-butenoate used as the starting material was prepared in a manner analogous to Example 7.

EXAMPLE 9

The isomerization complexes used in Examples 3-6 and 8 were prepared as follows:

604 mg (1.226 mmol) of di-μ-chloro-bis[η⁴-1,5-cyclooctadiene]dirhodium (I) were placed in a 50 ml Schlenk tube under argon and dissolved in 20 ml of absolute tetrahydrofuran. Thereto there was added dropwise from an injection syringe within 10 minutes while stirring a solution of 552.5 mg (2.452 mmol) of silver perchlorate monohydrate in 5 ml of absolute tetrahydrofuran. After stirring for a further 1 hour, the precipitated silver chloride was filtered off under argon. The turbid filtrate was left to stand until the remaining colloidal silver chloride which had passed through the frit had settled. The supernatant solution was then decanted off using an injection syringe and transferred into a Schlenk tube. To the clear yellow solution there was then added dropwise by means of a motor-driven syringe within 2 hours while stirring at room temperature a solution of 1.35 g (2.452 mmol) of (R)-(6,6'-dimethyl-2,2'-biphenylylene)-bis(diphenylphosphine) in 30 ml of absolute tetrahydrofuran, an orange precipitate resulting. The mixture was stirred for a further 1.5 hours, then filtered under argon and the filter residue was washed with 2 ml of tetrahydrofuran and dried briefly in a high vacuum. In this manner there were obtained 1.538 g of [η⁴-1,5-cyclooctadiene][(R)-(6,6'-dimethyl-2,2'-biphenylylene)-bis(diphenylphosphine)]-rhodium (I) perchlorate as an orange powder. Mutarotation was observed in the rotation determinations in dichloromethane and in acetonitrile.

1.101 g (2 mmol) of (S)-(6,6'-dimethyl-2,2'-biphenylylene)-bis(diphenylphosphine) were reacted in a manner analogous to the foregoing. 1.50 g of [η⁴-1,5-cyclooctadiene][(S)-(6,6'-dimethyl-2,2'-biphenylylene)-bis(diphenylphosphine)]rhodium (I) perchlorate were obtained as an orange powder. Mutarotation was observed in the rotation determination in chloroform. $[\alpha]_D^{20}$ (about 1 minute) = +20.5°; $[\alpha]_D^{20}$ (5 minutes) = −26.9° (c=0.464% in CHCl₃).

The (R)- or (S)-(6,6'-dimethyl-2,2'-biphenylylene)-bis(diphenylphosphine) used as the starting material was prepared according to Example 2 or in analogy to Example 2.

We claim:

1. An optically active bifunctional compound of the formula

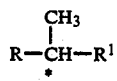

wherein R is a protected hydroxymethyl; and R¹ is

in which R² and R³ individually are lower alkyl or cycloalkyl or R² and R³ taken together with the nitrogen atom of Ia are a heterocyclic ring.

2. The compound of claim 1 wherein the compound is (1E,3R)-N,N-diethyl-4-tertiary butoxy-3-methyl-1-butenylamine.

3. The compound of claim 1 wherein the compound is (1E,3S)-N,N-diethyl-4-tertiary butoxy-3-methyl-1-butenylamine.

4. The compound of claim 1 wherein the compound is (1E,3S)-N,N-diethyl-4-benzyloxy-3-methyl-1-butenylamine.

5. The compound of claim 1 wherein the compound is (1E,3R)-4-benzyloxy-N,N-dibutyl-3-methyl-1-butenylamine.

6. The compound of claim 1 wherein the compound is 1-((1E,3R)-4-benzyloxy-3-methyl-1-butenyl)-piperidine.

7. The compound of claim 1 wherein the compound is 4-((1E,3R)-4-benzyloxy-3-methyl-1-butenyl)-morpholine.

8. The compound of claim 1 wherein the compound is (1E,3R)-N,N-diethyl-3-methyl-4-trimethylsiloxy-1-butenylamine.

9. The compound of claim 1 wherein the compound is (1E,3R)-N,N-diethyl-4-(methoxymethoxy)-3-methyl-1-butenylamine.

10. The compound of claim 1 wherein the compound is (1E,3R)-N,N-diethyl-3-methyl-4-(1-propenyloxy)-1-butenylamine.

* * * * *